US007824330B2

(12) United States Patent
Melanson

(10) Patent No.: US 7,824,330 B2
(45) Date of Patent: Nov. 2, 2010

(54) CERAMIC FIBER OPTIC TAPER HOUSING FOR MEDICAL DEVICES

(75) Inventor: Jeffrey S. Melanson, Sturbridge, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 1053 days.

(21) Appl. No.: 11/287,908

(22) Filed: Nov. 28, 2005

(65) Prior Publication Data

US 2007/0123752 A1    May 31, 2007

(51) Int. Cl.
    *A61B 1/07* (2006.01)
(52) U.S. Cl. .................. 600/182; 600/178; 362/554; 362/572; 362/574; 362/580
(58) Field of Classification Search .............. 600/129, 600/131, 132, 178, 179, 182; 362/554, 572, 362/574, 580
    See application file for complete search history.

(56) References Cited

U.S. PATENT DOCUMENTS

| 4,170,997 | A |   | 10/1979 | Pinnow et al. ............. 128/395 |
| 4,584,988 | A | * | 4/1986 | Nishioka et al. ............ 600/177 |
| 4,722,337 | A |   | 2/1988 | Losch et al. ............. 128/303.1 |
| 4,788,967 | A |   | 12/1988 | Ueda ............................. 128/6 |
| 5,380,277 | A |   | 1/1995 | Phillips ....................... 604/33 |
| 5,487,740 | A |   | 1/1996 | Sulek et al. .................... 606/15 |
| 5,651,759 | A | * | 7/1997 | Leiner et al. ................ 600/182 |
| 5,735,793 | A | * | 4/1998 | Takahashi et al. ........... 600/153 |
| 5,919,130 | A | * | 7/1999 | Monroe et al. .............. 600/200 |
| 5,960,145 | A | * | 9/1999 | Sanchez ..................... 385/116 |
| 6,010,450 | A | * | 1/2000 | Perkins ....................... 600/175 |
| 6,068,592 | A |   | 5/2000 | Davis .......................... 600/132 |
| 6,152,872 | A | * | 11/2000 | Peck et al. ................... 600/160 |
| 6,572,537 | B2 |  | 6/2003 | Futatsugi et al. ............ 600/133 |
| 6,692,432 | B1 | * | 2/2004 | Yarush et al. ................ 600/179 |
| 6,743,166 | B2 | * | 6/2004 | Berci et al. .................. 600/120 |
| 6,917,738 | B2 |  | 7/2005 | Guerra et al. ................ 385/117 |
| 6,942,372 | B1 | * | 9/2005 | Davis .......................... 362/580 |
| 7,290,915 | B2 | * | 11/2007 | Solovay et al. .............. 362/580 |
| 2002/0089586 | A1 | * | 7/2002 | Suzuki et al. .................. 348/68 |
| 2003/0130575 | A1 |  | 7/2003 | Desai .......................... 600/417 |
| 2004/0032751 | A1 | * | 2/2004 | Solovay et al. .............. 362/580 |
| 2004/0057250 | A1 | * | 3/2004 | Roberts et al. .............. 362/554 |
| 2004/0064019 | A1 | * | 4/2004 | Chang et al. ................ 600/180 |
| 2005/0276553 | A1 | * | 12/2005 | Kazakevich .................. 385/115 |

FOREIGN PATENT DOCUMENTS

JP          08160320 A   *   6/1996

* cited by examiner

*Primary Examiner*—Linda C Dvorak
*Assistant Examiner*—Samuel Candler
(74) *Attorney, Agent, or Firm*—St. Onge Steward Johnston & Reens LLC

(57) ABSTRACT

A system for transmitting the light required for a medical device is disclosed generally comprising an endoscope body, a light guide for transmitting light from a light source to the instrument body, where the light guide includes a bundle of optical fibers having a tapered portion, and a ceramic housing disposed around at least part of the tapered portion of the bundle. In certain embodiments, the ceramic has a pigment for improving insulation. In some embodiments, the taper and ceramic housing are located in an endoscope handle, which may be coupled to the endoscope body via an input post, and in certain embodiments, the inner diameter of the ceramic housing has an increase substantially equal to the decrease of diameter of the taper.

50 Claims, 2 Drawing Sheets

CERAMIC FIBER OPTIC TAPER HOUSING FOR MEDICAL DEVICES

FIELD OF THE INVENTION

The present invention relates to a system for transmitting the light required for a medical device. More specifically, the invention relates to a ceramic housing around a tapered portion of a fiber optic bundle for insulating other parts of the medical device from energy radiated therefrom.

BACKGROUND OF THE INVENTION

Systems for supplying light to a medical device in order to illuminate an area that a medical practitioner is viewing or working upon are generally well known in the art. For example, conventional endoscopes are often supplied with such a system.

Generally, an endoscope is a medical device for insertion into a body passageway or cavity that enables an operator to view and/or perform certain surgical procedures at a site inside a patient's body. As is known, endoscopes may be either rigid or flexible, and generally include a long tubular member equipped with, for example, a miniature viewing device, and in some cases, a working channel for a surgical instrument. The endoscope has a proximal end that remains external to the patient, from which the operator can view the site and/or manipulate a surgical instrument, and a distal end having an endoscope tip for insertion into the body cavity of the patient.

In order to facilitate proper operation, the endoscope typically includes a source of light for illuminating the area the medical practitioner is trying to view and/or work upon. This illumination is usually supplied by an external light source, which typically comprises high powered lamps, such as, for example, a Xenon lamp. Light is transmitted from this light source to the distal portion of the endoscope inserted in the body by a waveguide, such as a fiber optic light cable, in order to guide the light to the scope. Such cables typically incorporate a fiber optic bundle, which comprises a plurality of thin optical fibers made of glass or optical plastic.

A general disadvantage of some scopes of this type is that the transfer of energy from these light sources through these light guides can cause undesired heating of the exterior components of the device. Conventional remedies for this problem involve the use of an infrared filter for the light source. However, in cases where large amounts of energy are involved, undesired heating can still occur even in the absence of excessive infrared radiation.

As further described herein, it is desirable to use in some endoscopes a fiber optic bundle that has a tapered section, for several reasons. First, the use of a taper allows the light guide to receive the light from the external light source at a low numerical aperture and then increase the numerical aperture in order to enlarge the light angle. Second, the taper allows the light to be received at a large diameter, and then reduces this diameter and increases the power density.

However, a disadvantage of these arrangements is that there is a significant loss of power that radiates from the external glass surface of the taper. This contributes significantly to the generation of undesirable heat as discussed above.

Additionally, another disadvantage of these arrangements is that this thinner section of the fiber optic bundle is even more prone to breaking or fracturing during assembly of the instrument.

What is desired, therefore, is a system for transmitting the light required for a medical device that can increase the numerical aperture of the light and can increase the power density of the light. What is further desired is a system for transmitting this light that does not transfer excessive heat to the exterior components of the medical device. What is also desired is a system for transmitting this light that does not easily become damaged during assembly.

SUMMARY OF THE INVENTION

Accordingly, it is an object of the present invention to provide a system for transmitting the light required for a medical device where the diameter of a portion of the light path decreases.

It is a further object of the present invention to provide a system for transmitting the light required for a medical device that insulates the exterior components of the device from energy radiated from the light guide transmitting the light.

It is yet another object of the present invention to provide a system for transmitting the light required for a medical device that is protected from breakage.

In order to overcome the deficiencies of the prior art and to achieve at least some of the objects and advantages listed, the invention comprises a medical device, including an endoscope body, a light source, a light guide for transmitting light from the light source to the endoscope body, wherein the light guide comprises a bundle of optical fibers, the bundle having a tapered portion, and a ceramic housing disposed around at least part of the tapered portion of the bundle.

In another embodiment, the invention comprises a medical device, including, an instrument body, a light guide for transmitting light to the instrument body, wherein the light guide comprises a bundle of optical fibers, the bundle having a tapered portion, and a ceramic housing disposed around at least part of the tapered portion of the bundle.

In yet another embodiment, the invention comprises a medical device, including a housing, a fiber optic bundle for transmitting light disposed in the housing, wherein the bundle includes a tapered portion for altering an attribute of the light transmitted therethrough, and a ceramic disposed around at least part of the tapered portion of the bundle for at least partially insulating the housing from energy radiating from the tapered portion of the bundle.

In some embodiments, the bundle includes an outer surface having a diameter that decreases in the direction of light transmission, the ceramic housing has an inner surface adjacent the outer surface of the bundle that increases in the direction of light transmission, and the diameter increase of the inner surface of the ceramic housing is substantially equal to the diameter decrease of the outer surface of the bundle.

In certain embodiments, where the device is an endoscope, the ceramic housing is located in a handle coupled to the endoscope body. In some of these embodiments, the endoscope body has an input post extending away from the longitudinal axis of the body in a radial direction, and the handle is coupled to the endoscope body via the input post.

DETAILED DESCRIPTION OF THE INVENTION

Figure 1:
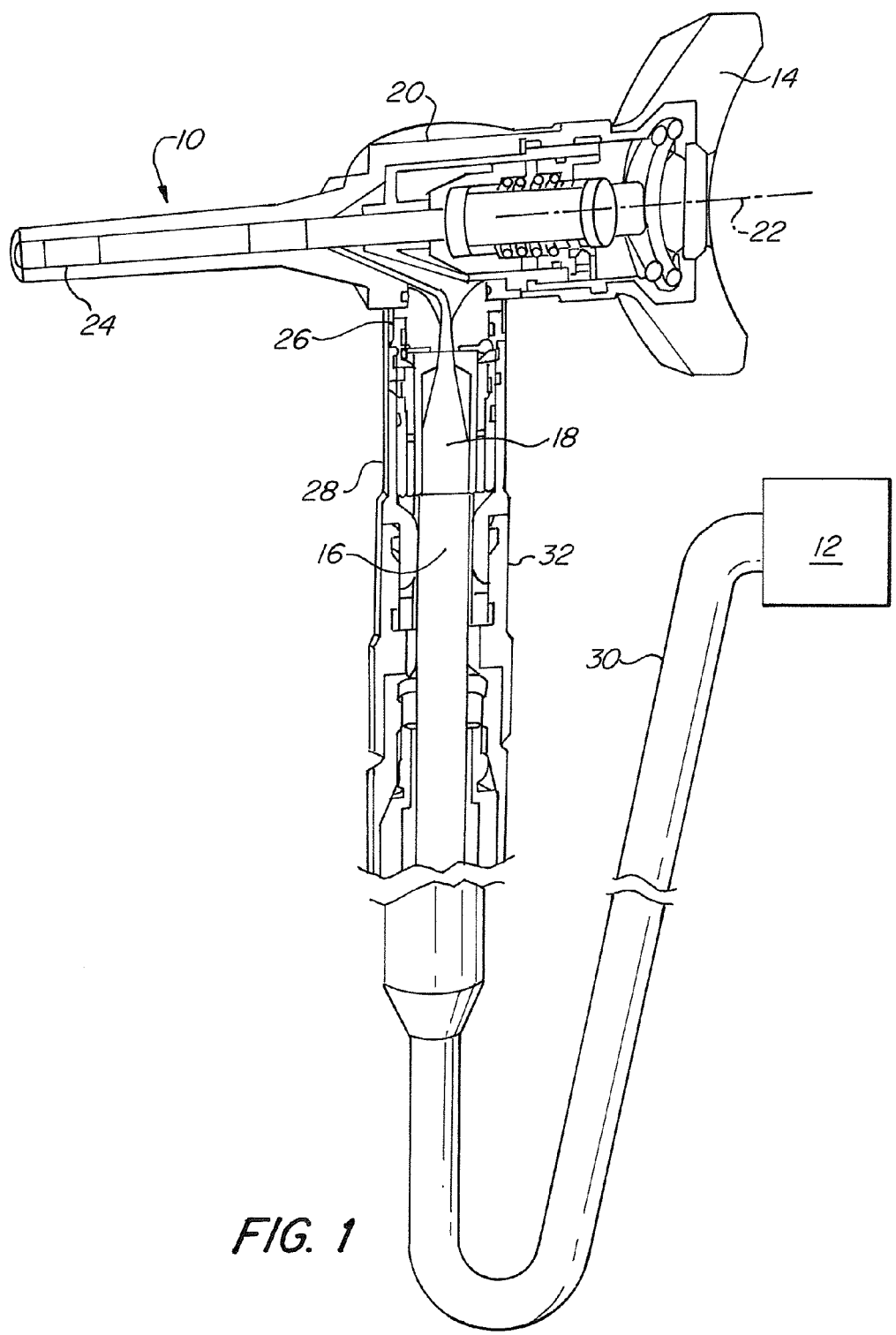
FIG. 1 is a partially cut-away, isometric view of an endoscopic system in accordance with the invention.

The basic components of one embodiment of a system 10 for transmitting the light required for a medical device in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system 10 includes a light source 12 such as, for example, a 300 watt Xenon lamp, for generating a light beam. The light source 12 is connected to a medical device 14, such as an endoscope, via a light guide 16, such as a bundle of optical fibers 18 that collectively operate as a waveguide for the light supplied by the source 12. This bundle 18 is housed within at least one outer housing, typically in the form of a cable 30 connected to the source 12 or a portion of the instrument, such as light guide stem 28, which may, in some embodiments, also serve as a handle. It should be noted, however, that in other embodiments, a separate handle (not shown), separate from the light guide stem 28, may be provided.

The endoscope 14 includes an elongated endoscope body 20 having a longitudinal axis 22, which houses various mechanical, electrical and optical components, and includes a flexible insertion shaft 24 that extends from the body 20. The endoscope body 20 further includes an input post 26 that extends away from the longitudinal axis 22 in a radial direction. A handle 28 is coupled to the endoscope body 20 via the input post 26. The fiber optic cable 30 is, in turn, connected to the handle 28, usually via a detachable coupling 32. By this arrangement, the light beam is transmitted from the source 12 to the endoscope 14 via the fiber optic bundle 18.

Figure 2:
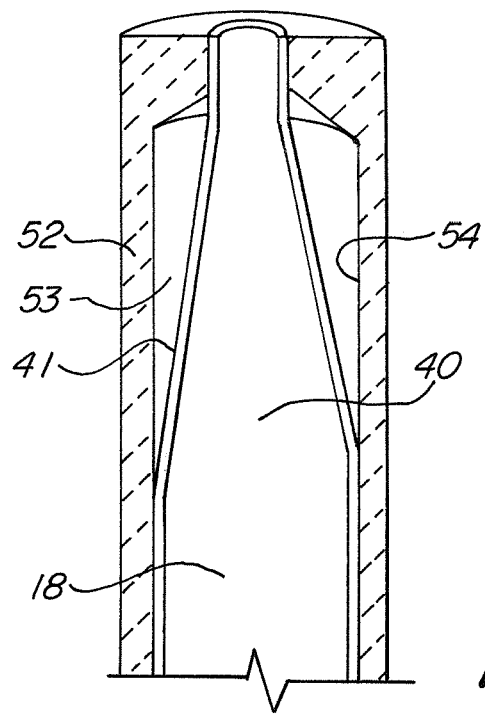
FIG. 2 is a partially cut-away, isometric view in partial cross-section showing additional detail of the fiber optic bundle and ceramic housing of the system of FIG. 1.

As shown more clearly in FIG. 2, the fiber optic bundle 18 includes a tapered portion 40 for altering at least one attribute of the light transmitted therethrough. Accordingly, the outer surface 42 of this portion of the bundle 18 decreases in the direction in which the light is transmitted. As a result, the numerical aperture of the light transmitted therethrough is increased. Additionally, by using this arrangement, the diameter of the light beam, which originally is large, can be decreased prior to transmission through the necessarily thin insertion shaft 24, simultaneously increasing the power density of the light.

A ceramic 52 is disposed around at least part of the tapered portion 40, thereby insulating other components of the device from energy radiating from this portion of the bundle 18, and, in some embodiments, is disposed around the entire taper 40. Accordingly, the space between the outer housing in which the taper resides—such as handle 28—is filled with ceramic, such that the rate of heat transfer from the tapered portion 40 to the handle 28 is sufficiently slowed in order to allow the handle 28 to operate as an efficient heat sink.

It should be noted that, though the tapered portion 40 as depicted in the drawings and described herein is located within an endoscope handle 28, in other embodiments, the tapered portion 40 may exist in other portions of light guide 16, and thus, may be disposed within other types of housings. For example, in some embodiments, the tapered portion may simply be located along a portion of a cable 30 leading directly to the device 14.

Figure 3:
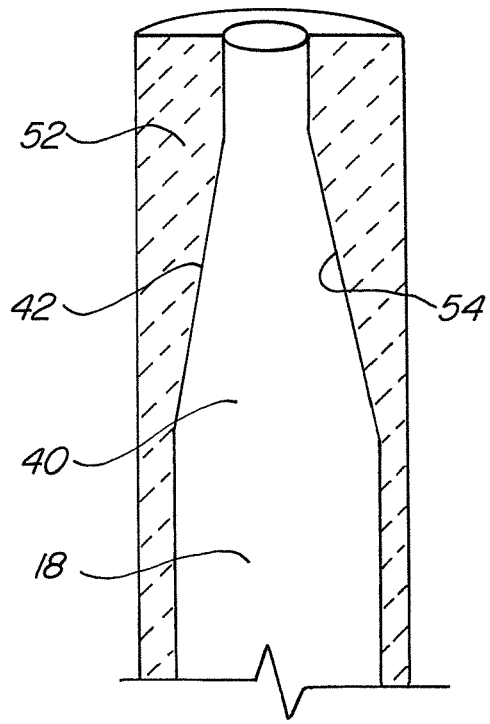
FIG. 3 is a partially cut-away, isometric view in partial cross-section showing additional detail of the fiber optic bundle and ceramic housing of the system of FIG. 1.

As shown in FIG. 2, in some embodiments, a gap 53 exists between the taper and the inner surface 54 of the ceramic 52, which may be preferable for machining purposes. As illustrated in FIG. 3, in other advantageous embodiments, the inner surface 54 of the ceramic housing 52 is adjacent the outer surface 42 of the taper 40 and decreases in the direction in which the light is transmitted therethrough, such that the increase in diameter of the ceramic housing 52 is substantially equal to the decrease in diameter of the tapered portion 40. Regardless of the correspondence between surfaces 42 and 54, however, the ceramic housing 52 is shaped such that an upper section of ceramic 52 provides a thermal break between the tapered portion 40 and the input post 26 and endoscope body 20.

Additionally, the ceramic housing 52 serves as a protective shell for the tapered portion 40, which is otherwise more vulnerable to fractures or breaks due to it's thinning diameter.

The housing 52 may be comprised of any ceramic with good insulative properties, such as, for example, Macor®, alumina silicate, steatite, alumina bisque, zirconia phosphate, or cordierite. In some embodiments, an additional ceramic paint or coating 41 may be applied to the outer surface 42 of the taper to provide further insulation. The ceramic may exist in either a fired or non-fired state. In certain advantageous embodiments, the ceramic 52 has a pigment, such as a light gray or brown color, in order to maximize the insulative properties of the ceramic against both light and heat.

In certain advantageous embodiments, the bundle 18 is affixed to the ceramic housing 52 with a durable adhesive. In some of these embodiments, this adhesive is non-conductive in order to further maximize insulation.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A medical device, comprising:
an endoscope body;
a light source;
a light guide for transmitting light from said light source to said endoscope body;
wherein said light guide comprises a bundle of optical fibers, said bundle having a tapered portion, wherein said bundle includes an outer surface having a diameter that decreases in the direction of light transmission; and
a ceramic housing disposed around at least part of the tapered portion of said bundle.

2. The device of claim 1, wherein said ceramic housing has an inner surface adjacent the outer surface of said bundle, the inner surface of said housing having a diameter that increases in the direction of light transmission.

3. The device of claim 2, wherein the diameter increase of the inner surface of said ceramic housing is substantially equal to the diameter decrease of the outer surface of said bundle.

4. The device of claim 1, further comprising a handle coupled to said endoscope body, wherein said ceramic housing is located in said handle.

5. The device of claim 4, wherein:
said endoscope body has a longitudinal axis and includes an input post extending away from said axis in a radial direction; and said handle is coupled to said endoscope body via said input post.

6. The device of claim 1, wherein said ceramic has a pigment for improving insulation.

7. The device of claim 1, wherein said light source is a Xenon lamp.

8. A medical device, comprising:
an instrument body;
a light guide for transmitting light to the instrument body;
wherein said light guide comprises a bundle of optical fibers, said bundle having a tapered portion, wherein said bundle includes an outer surface having a diameter that decreases in the direction of light transmission; and
a ceramic housing disposed around at least part of the tapered portion of said bundle.

9. The device of claim 8, wherein said body includes an endoscope body.

10. The device of claim 9, further comprising a handle coupled to said endoscope body, wherein said ceramic housing is located in said handle.

11. The device of claim 10, wherein:
said endoscope body has a longitudinal axis and includes an input post extending away from said axis in a radial direction; and
said handle is coupled to said endoscope body via said input post.

12. The device of claim 8, wherein said ceramic housing is disposed along the whole length of the tapered portion of said bundle.

13. The device of claim 8, wherein said ceramic housing has an inner surface adjacent the outer surface of said bundle, the inner surface of said housing having a diameter that increases in the direction of light transmission.

14. The device of claim 13, wherein the diameter increase of the inner surface of said ceramic housing is substantially equal to the diameter decrease of the outer surface of said bundle.

15. The device of claim 8, wherein said ceramic has a pigment for improving insulation.

16. A medical device, comprising;
a housing;
a fiber optic bundle for transmitting light disposed in said housing;
wherein said bundle includes a tapered portion for altering an attribute of the light transmitted therethrough, wherein said bundle includes an outer surface having a diameter that decreases in the direction of light transmission; and
a ceramic disposed around at least part of the tapered portion of said bundle for at least partially insulating the housing from energy radiating from the tapered portion of said bundle.

17. The instrument of claim 16, wherein said housing comprises a light cable.

18. The instrument of claim 16, wherein said ceramic housing has an inner surface adjacent the outer surface of said bundle, the inner surface of said housing having a diameter that increases in the direction of light transmission.

19. The instrument of claim 18, wherein the diameter increase of the inner surface of said ceramic housing is substantially equal to the diameter decrease of the outer surface of said bundle.

20. The instrument of claim 16, wherein said ceramic has a pigment for improving insulation.

21. A medical device, comprising:
an endoscope body;
a light source;
a light guide for transmitting light from said light source to said endoscope body;
wherein said light guide comprises a bundle of optical fibers, said bundle having a tapered portion; and
a ceramic housing disposed around at least part of the tapered portion of said bundle, wherein said ceramic has a pigment for improving insulation.

22. The device of claim 21, wherein said bundle includes an outer surface having a diameter that decreases in the direction of light transmission, and wherein said ceramic housing has an inner surface adjacent the outer surface of said bundle, the inner surface of said housing having a diameter that increases in the direction of light transmission.

23. The device of claim 22, wherein the diameter increase of the inner surface of said ceramic housing is substantially equal to the diameter decrease of the outer surface of said bundle.

24. The device of claim 21, further comprising a handle coupled to said endoscope body, wherein said ceramic housing is located in said handle.

25. The device of claim 24, wherein:
said endoscope body has a longitudinal axis and includes an input post extending away from said axis in a radial direction; and
said handle is coupled to said endoscope body via said input post.

26. The device of claim 21, wherein said light source is a Xenon lamp.

27. A medical device, comprising:
an instrument body;
a light guide for transmitting light to the instrument body;
wherein said light guide comprises a bundle of optical fibers, said bundle having a tapered portion; and
a ceramic housing disposed around at least part of the tapered portion of said bundle, wherein said ceramic has a pigment for improving insulation.

28. The device of claim 27, wherein said body includes an endoscope body.

29. The device of claim 28, further comprising a handle coupled to said endoscope body, wherein said ceramic housing is located in said handle.

30. The device of claim 29, wherein:
said endoscope body has a longitudinal axis and includes an input post extending away from said axis in a radial direction; and
said handle is coupled to said endoscope body via said input post.

31. The device of claim 27, wherein said ceramic housing is disposed along the whole length of the tapered portion of said bundle.

32. The device of claim 27, wherein said bundle includes an outer surface having a diameter that decreases in the direction of light transmission, and wherein said ceramic housing has an inner surface adjacent the outer surface of said bundle, the inner surface of said housing having a diameter that increases in the direction of light transmission.

33. The device of claim 32, wherein the diameter increase of the inner surface of said ceramic housing is substantially equal to the diameter decrease of the outer surface of said bundle.

34. A medical device, comprising;
a housing;
a fiber optic bundle for transmitting light disposed in said housing;
wherein said bundle includes a tapered portion for altering an attribute of the light transmitted therethrough; and a ceramic disposed around at least part of the tapered portion of said bundle for at least partially insulating the housing from energy radiating from the tapered portion of said bundle, wherein said ceramic has a pigment for improving insulation.

35. The instrument of claim 34, wherein said housing comprises a light cable.

36. The instrument of claim 34, wherein said bundle includes an outer surface having a diameter that decreases in the direction of light transmission, and wherein said ceramic housing has an inner surface adjacent the outer surface of said bundle, the inner surface of said housing having a diameter that increases in the direction of light transmission.

37. The instrument of claim 36, wherein the diameter increase of the inner surface of said ceramic housing is substantially equal to the diameter decrease of the outer surface of said bundle.

38. A medical device, comprising:
an endoscope body;
a light source;
a light guide for transmitting light from said light source to said endoscope body;
wherein said light guide comprises a bundle of optical fibers, said bundle having a tapered portion;
a ceramic housing disposed around at least part of the tapered portion of said bundle; and
a handle coupled to said endoscope body, wherein said ceramic housing is located in said handle.

39. The device of claim 38, wherein said bundle includes an outer surface having a diameter that decreases in the direction of light transmission, and wherein said ceramic housing has an inner surface adjacent the outer surface of said bundle, the inner surface of said housing having a diameter that increases in the direction of light transmission.

40. The device of claim 39, wherein the diameter increase of the inner surface of said ceramic housing is substantially equal to the diameter decrease of the outer surface of said bundle.

41. The device of claim 38, wherein:
said endoscope body has a longitudinal axis and includes an input post extending away from said axis in a radial direction; and
said handle is coupled to said endoscope body via said input post.

42. The device of claim 38, wherein said light source is a Xenon lamp.

43. A medical device, comprising:
an instrument body, wherein said body includes an endoscope body;
a light guide for transmitting light to the instrument body;
wherein said light guide comprises a bundle of optical fibers, said bundle having a tapered portion;
a ceramic housing disposed around at least part of the tapered portion of said bundle, wherein said ceramic has a pigment for improving insulation; and
a handle coupled to said endoscope body, wherein said ceramic housing is located in said handle.

44. The device of claim 43, wherein:
said endoscope body has a longitudinal axis and includes an input post extending away from said axis in a radial direction; and
said handle is coupled to said endoscope body via said input post.

45. The device of claim 43 wherein said ceramic housing is disposed along the whole length of the tapered portion of said bundle.

46. The device of claim 43, wherein said bundle includes an outer surface having a diameter that decreases in the direction of light transmission, and wherein said ceramic housing has an inner surface adjacent the outer surface of said bundle, the inner surface of said housing having a diameter that increases in the direction of light transmission.

47. The device of claim 46, wherein the diameter increase of the inner surface of said ceramic housing is substantially equal to the diameter decrease of the outer surface of said bundle.

48. A medical device, comprising;
a housing;
a fiber optic bundle for transmitting light disposed in said housing;
wherein said bundle includes a tapered portion for altering an attribute of the light transmitted therethrough; and
a ceramic disposed around at least part of the tapered portion of said bundle for at least partially insulating the housing from energy radiating from the tapered portion of said bundle, wherein said ceramic has a pigment for improving insulation;
wherein said housing comprises a light cable.

49. The instrument of claim 48, wherein said bundle includes an outer surface having a diameter that decreases in the direction of light transmission, and wherein said ceramic housing has an inner surface adjacent the outer surface of said bundle, the inner surface of said housing having a diameter that increases in the direction of light transmission.

50. The instrument of claim 48 wherein the diameter increase of the inner surface of said ceramic housing is substantially equal to the diameter decrease of the outer surface of said bundle.

* * * * *